(12) United States Patent
Medina Rivero

(10) Patent No.: US 11,471,552 B2
(45) Date of Patent: Oct. 18, 2022

(54) PERFUME TESTERS

(71) Applicant: AIRPARFUM TIMELESS, S.L., Bollullos de la Mitacion (ES)

(72) Inventor: Armando Medina Rivero, Seville (ES)

(73) Assignee: AIRPARFUM TIMELESS, S.L., Bollullos de la Mitacion (ES)

(*) Notice: Subject to any disclaimer, the term of this patent is extended or adjusted under 35 U.S.C. 154(b) by 543 days.

(21) Appl. No.: 16/474,031

(22) PCT Filed: Dec. 28, 2017

(86) PCT No.: PCT/EP2017/084772
§ 371 (c)(1),
(2) Date: Jun. 26, 2019

(87) PCT Pub. No.: WO2018/122350
PCT Pub. Date: Jul. 5, 2018

(65) Prior Publication Data
US 2019/0388576 A1 Dec. 26, 2019

(30) Foreign Application Priority Data
Dec. 29, 2016 (WO) .................. PCT/ES2016/070946

(51) Int. Cl.
*A61L 9/14* (2006.01)
*G01N 1/22* (2006.01)

(52) U.S. Cl.
CPC .................. *A61L 9/14* (2013.01); *G01N 1/22* (2013.01); *A61L 2209/11* (2013.01); *A61L 2209/131* (2013.01); *A61L 2209/133* (2013.01)

(58) Field of Classification Search
CPC .. A61L 9/14; A61L 2209/11; A61L 2209/131; A61L 2209/133; A61L 9/127; G01N 1/22
See application file for complete search history.

(56) References Cited

U.S. PATENT DOCUMENTS

| 2,608,436 A | 8/1952 | Baughman |
| 5,725,152 A | 3/1998 | Akyu |

(Continued)

FOREIGN PATENT DOCUMENTS

| BE | 1016187 A6 | 4/2006 | |
| EP | 1108437 A1 * | 6/2001 | ............. A61L 9/127 |

(Continued)

OTHER PUBLICATIONS

International Search Report and Written Opinion dated Apr. 20, 2018 for Application No. PCT/EP2017/084772, 12 pages.

*Primary Examiner* — Sean E Conley
*Assistant Examiner* — Brendan A Hensel
(74) *Attorney, Agent, or Firm* — Squire Patton Boggs (US) LLP

(57) ABSTRACT

Perfume testers comprising one or more atomizers are disclosed. The atomizer comprises a liquid compartment and a mixing compartment. The mixing compartment comprises an air inlet and an air outlet. The mixing compartment comprises a mixing opening facing the liquid compartment and the liquid compartment comprises a liquid opening facing the mixing compartment. The mixing opening matches the liquid opening. The atomizer further comprises a wick connecting the liquid compartment and the mixing compartment such that in use the wick fits in the liquid and mixing compartments openings in an airtight manner. The wick extends into the mixing and liquid compartments. A portion of the wick extending into the mixing compartment comprises an outer contact surface and a volume of the mixing compartment is defined such that a ratio between the outer contact surface and the volume of the mixing compartment is at least approximately 0,05:1.

17 Claims, 7 Drawing Sheets

(56) References Cited

U.S. PATENT DOCUMENTS

| | | |
|---|---|---|
| 6,371,451 B1 | 4/2002 | Choi |
| 2002/0153622 A1 | 10/2002 | Hugon |
| 2005/0195366 A1 | 9/2005 | Selander et al. |
| 2005/0212151 A1 | 9/2005 | Malle |
| 2007/0295831 A1* | 12/2007 | Ward .................. A01M 1/2044 239/47 |
| 2010/0288847 A1* | 11/2010 | Gruenbacher .......... A61L 9/122 239/34 |
| 2011/0290908 A1* | 12/2011 | Tranzeat ............. A01M 1/2033 239/44 |

FOREIGN PATENT DOCUMENTS

| | | |
|---|---|---|
| EP | 1108437 A1 | 6/2001 |
| FR | 2944705 A1 | 10/2010 |
| JP | H0638996 U | 5/1994 |
| KR | 100716609 B1 | 5/2007 |
| WO | WO 2004/009142 A1 | 1/2004 |
| WO | WO 2004/096299 A1 | 11/2004 |
| WO | WO 2008/032268 A1 | 3/2008 |
| WO | WO 2014/154909 A1 | 10/2014 |

\* cited by examiner

PERFUME TESTERS

This application is a 35 U.S.C. 371 filing of International Application No. PCT/EP2017/084772, filed on Dec. 28, 2017, which claims priority to and the benefit of International Patent Application No. PCT/ES2016/070946, filed on Dec. 29, 2016, all of which are incorporated verbatim herein by reference in their entirety, including the specifications, drawings, and the claims.

The present disclosure refers to a device allowing testing of one or more perfumes, eau de perfumes, colognes, eau de colognes or fragrances in general in liquid state, their compositions including alcohol or other volatile or highly volatile compounds.

BACKGROUND

Reviewing solutions already existing in the market, there are a wide variety of oil perfumes with an operation analogous to that of air fresheners. The aforementioned air fresheners when perfuming the environment by direct evaporation thus have a much simpler operation which consist in leaving them open and regulate the contact with the air, even the most advanced models. To do this some air fresheners incorporate resistances, others have fans and even the more innovative ones use steam by ultrasonic or actuate one or more sprays by a mechanical drive. However the present disclosure is aimed at solving a completely different problem being applied mainly to volatile or highly volatile perfumes.

Considering perfume testers characterized by containing in their composition alcohol or other volatile or highly volatile compounds, existing solutions just like air fresheners are based on squeezing the atomizer of a bottle of perfumes with a mechanical element. In general, these are complex and impractical designs which also involve too many components and in most cases try to spray the perfume in some way.

Perfume tests are generally performed by spraying the perfume directly on a piece of paper strip or composite material strip called "mouillettes" or blotters, or spraying on the person performing the test. Considering the problems of this traditional type of tests, the most relevant is that the perfume in its initial phase contains a high alcohol content which does not allow its odor to be adequate for a satisfactory testing. This way, what should be a simple movement to test a perfume becomes a complex procedure to choose a perfume among various that are being presented.

Another not least drawback is that there is a high risk that the test is unsuccessful as a result of a physical contact with the perfume thereby the perfume could remain attached to some part of the body, mainly the nose, causing mixtures between the different perfumes to be tested. Finally, it is also remarkably the saturation caused by smelling a perfume with an inadequate intensity or with a high content of alcohol up to the point that in these cases it is better to abandon the selection process for a long period of time. In fact, perfume experts do not recommend testing more than three perfumes one after the other.

Considering the state of the art, there are several disclosures which try to improve the aforementioned system, without reaching the sufficient technical simplicity, quality or veracity required by a test of one of the most valued and expensive compounds in the world.

Specifically, patent U.S. Pat. No. 6,568,659 B2, proposes a model formed by several components or fixed parts in which it can mainly be highlighted that unlike the present design that separates the perfume container and the transmitter and mixer element by making fix these last parts in the device with the intention of replacing the container bottle of a perfume only without considering the irreversible contamination that the fixed part of the device would have and the difficulty of accessing these parts in the event that it were necessary. The total pulverization of the perfume in the air is also not guaranteed, being able to drag small drops of the same as it projects said air on a mesh impregnated with perfume without having absolute control over the amount of perfume that is adhered to the mesh, particularly to the face opposite from where the air is projected and that would lodge part of the perfume without being affected by the reticle to which it would be subjected by the mesh itself. In spite of the complexity, the high volatility of a perfume is not solved as it does not contemplate elements that guarantee the tightness of the system. Unlike our design that is based on a single mixer atomizer air perfume element and container of the same that encompasses the entire base of operation thereby facilitating the installation, replacement and manipulation of the device, therefore being reduced to a minimum the fixed parts to which there is total accessibility in addition to a e.g. cleaning and deodorization system by ozone gas that makes it easy to replace one perfume with another without having to replace any fixed element of the device.

The patent U.S. Pat. No. 7,419,535 B2 discloses a similar application to that proposed with the present disclosure. However the technical solution is so complex and it is even not effective for what it is intended. One clear drawback of this design is the lack of knowledge of the perfume composition, which is composed of fixers that adhere to any surface in addition to a high volatility. This design does not give importance to this fact as it provides a path for the perfume through the different common pipes which would achieve pipes impregnated with the perfume. This design even leaves a common volume where the wastes that could be generated as a result of a possible condensation or excess of perfume. This, in practice, would provide mixtures of different odours when substituting or changing the perfume or even they would have a very negative impact over time, especially by the common exit design where all the fragrances would be mixed. The total pulverization of the perfume is also not contemplated in this design since the way of producing the mixture according to this disclosure consists in elevating by capillarity the perfume by means of a tube installed in a second tank where said perfume is housed and directing air under pressure to the mouth of said tube causing a spray or dispersion of the perfume to be dragged by an air stream and take it outside without offering a solution to the possibility that a drop of perfume may be directed to the face, particularly the eyes, of the users. As adjustment measures they use different air streams generated by at least two devices passing through different air streams and arranging valves in their path thereby making their adjustment very complicated and incomprehensible to the point that it is mentioned that such adjustments would be made when the device is installed.

Similarly, the International patent application publication number WO2014068159, also refers to a fragrance tester, but in this case it is limited to directly pumping the perfume in liquid state and spraying it on some part of the body of the user, the process not being clearly explained. Although this design results in a conventional test, it is worth mentioning the use of computer means as an example of automation for a better performance. However, they are not used as in our design for an adjustment that allows varying or adjusting the result of the tests.

Finally, in the French patent application publication number FR2677870A1, reference is also made to a fragrance tester, but in this case it is focused on food and beverages even proposing a game consisting in relating a certain smell to the food or beverage being considered among some variables proposed as solutions. The meaning of this patent is confirmed, as it even proposes a scoring system based on hits and misses. Regarding the state of the art, it basically consists in opening a container by means of electrically operated mechanical elements, allowing its content to be directly smelled and then closing it. It has nothing to do with our design as although it superficially mentions pressures and solenoids in this case, they are used with the aim of pressurizing the container containing the food or beverages and not as elements intervening in the generation or composition of the odors.

Document WO2008/032268 discloses a dispenser or diffuser assembly for dispensing or diffusing at least one composition comprising at least two independent refills, each comprising a reservoir containing a composition to be diffused and an electronic memory.

Document JPH0638996 discloses air fresheners having a wick that protrudes upwards from an open portion of a fragrance container and that enters a space portion inside a lid element.

Focusing the problem to be solved it is important to consider how the perfume is considered as "art" where a few are considered as the best perfumers in the world, capable of creating fragrances that will make history. These perfumers are called "nose" and currently there is a ranking with the best "noses" in the world, who act as judges of a competition to enter in the list of the creators of the best perfumes in the world throughout the history.

In this context and as a summary, there is a need to find answers to the following difficulties:

a) High volatility: it is about preventing the perfume from evaporating, making its housing stagnant.

b) Mixing air with perfume: this is apparently easy to do. However, no one has successfully addressed it in a simple manner, thus making it possible to function efficiently.

c) Avoiding excess of alcohol in the mixture with air: key aspect where designs fail or get so complex to unfeasible designs, in order to be implemented in stores specialized in selling perfumes which is its natural site.

d) Avoiding liquids, particularly droplets in the mixture: it should be ensured that this does not happen as it would cause the saturation the present disclosure intends to avoid, as well as a high probability that the perfume reaches the user's eyes in a liquid state.

e) Adjustments in the mixture: the design cannot be as complicated as a carburetor that includes movable elements, but one must consider the possibility of adjusting the density with which a perfume is to be shown/tested, depending on which density its creator or merchant considers more appropriate. Put in other words, there is a need for a simple design in which a concentration of perfumery ingredients can be adjusted.

f) Air flow: logically if one talks about perfumed air there is a flow or volume variable, which together with the referred density or concentration of perfumery ingredients, vary the perception of a perfume by the user.

g) Air temperature: since the perfume changes its smell depending on the temperature at which it is exposed, it is interesting as well as innovative to consider this factor.

h) Avoiding mixtures of different perfumes: the issue is that perfumes contain fats or fixers to facilitate their adherence to the human body, so any element through which it passes may be contaminated, making especially complicated the common parts or the changes of fragrance by passing them through an already used conduit.

i) Equalising the test: the challenge to be tackled consists in making equal the test independently of the place where it is performed. The creators or large perfume companies are the most interested in such a valuable product being treated as they deem appropriate. This is where above mentioned adjustments come into play.

j) Simplicity for the manufacturer or creator: choice, control and adjustments may be pre-established by the manufacturer or creator by providing an appropriate atomizer that may even be a single use one and at a very competitive price, based on the simplicity of its design and the use of very common materials.

k) Simplicity for the merchant: care should be taken not to provide equipment that requires a specialization each time it has to be manipulated. It must be simple and logical.

l) Simplicity for the end user: this is only possible if the result of the whole assembly provides a test of an adequate quality, for example, by being able to successfully perform in a usual manner the test of ten perfumes in less than a minute.

m) Preservation of the perfume: perfume is an extremely delicate element, in particular it is affected by contact with air, causing its components to oxidise thereby causing irreversible deterioration as well as an alteration of the smell in question.

SUMMARY

In a first aspect, an atomizer for alcoholic or hydro-alcoholic liquids is provided. The atomizer comprises a liquid compartment configured to receive a liquid and a mixing compartment provided next to the liquid compartment. The mixing compartment comprises an air inlet and an air outlet. The mixing compartment comprises a mixing opening facing the liquid compartment and the liquid compartment comprises a liquid opening facing the mixing compartment. The mixing opening matches the liquid opening. The atomizer further comprises a wick connecting the liquid compartment and the mixing compartment such that in use the wick fits in the liquid compartment opening and in the mixing compartment opening in an airtight manner, the wick extending into the mixing and liquid compartments. A portion of the wick extending into the mixing compartment comprises an outer contact surface and a volume of the mixing compartment is defined such that a ratio between the outer contact surface and the volume of the mixing compartment is at least approximately 0,05:1. Particularly a ratio of at least approximately 0,4:1 may be foreseen. More particularly a ratio of at least approximately 1:1. Put in other words, the ratio outer contact surface/volume of the mixing compartment is at least approximately 0,05 $mm^{-1}$, particularly at least approximately 0,4 $mm^{-1}$, more particularly at least approximately 1 $mm^{-1}$.

Throughout the present description and claims an atomizer should be understood as a device configured to mix a certain amount of liquid, particularly perfume ingredients from an alcohol/hydro-alcohol based perfume composition with an air flow and to blow the perfumed air stream through an outlet e.g. towards the face of a user. The use of "atomizer" is based on its ample definition of a device that reduces liquids to a fine spray. As will be explained in the following paragraphs the term "fine spray" should be considered as a gas, particularly a scented gas, essentially free of an aerosol mist of liquid particles or with imperceptible droplets, as if it were a diffuser combined with an air stream.

Throughout the present description and claims alcoholic or hydro-alcoholic liquids should be understood as liquids containing alcohol thereby rendering a highly volatile composition. Particularly, alcoholic or hydro-alcoholic perfumes should be distinguished from aromatic solutions containing oils. Examples of hydro-alcoholic compositions may include EDP, EDT and/or EDC among others. In some examples, alcoholic or hydro-alcoholic liquids may have at least 60% alcohol by volume (ABV).

Throughout the present description and claims the wick in use means that it is flooded with the liquid contained in the liquid compartment. Put in other words, it is a fully saturated wick. Moreover, a wick is to be understood as a porous medium able to spontaneously draw off liquid by capillary action (wicking).

According to this aspect, an atomizer or diffuser combined with an air stream is provided that includes a particular ratio between the wick's outer contact surface in use, i.e. when flooded, and the volume of the mixing compartment into which it is projected. Such a ratio takes into account the two main physical phenomena occurring inside the atomizer/diffuser, particularly inside the mixing compartment, when it is being used with alcoholic or hydro-alcoholic liquids. On one hand, the fact that alcoholic or hydro-alcoholic liquids/compositions, for example hydro-alcoholic perfumes, are highly volatile compositions and thus, when they are surrounded by a closed volume, space or compartment they evaporate inside such a volume, space or compartment. In addition, the first ingredients that evaporate are the most volatile ones, i.e. the alcohol. This way, the amount of liquid evaporated inside such a volume, space or compartment in between tests increases as the volume, space or compartment surrounding the liquid increases. Particularly, in this case, since the perfume is provided through the flooded wick, the volume surrounding the perfume is indeed the mixing compartment. Having an amount of liquid already evaporated (and mostly containing alcohol) do alter successive tests.

On the other hand, the fact that the rate of e.g. perfumery components that evaporate from a wick flooded with a hydro-alcoholic perfume increases as the contact surface gets larger. This way, the claimed ratios guarantee that the volume inside which the wick (flooded with alcoholic/hydro-alcoholic perfume) is disposed is sufficiently small to avoid or at least reduce undesired volatilizations of the perfume (particularly of the most volatile components of the perfume, i.e. alcohol), e.g. when there is no air stream circulating through the air inlet, i.e. inside the mixing compartment. This means that substantially no residual odours (or negligible odours) are present in the mixing compartment when there is no air stream. Put in other words, this avoids or at least reduces contaminations in between successive tests. Moreover, the fact of confining the wick in such a small volume, i.e. practically without air, guarantees that in any case, residual odours left in between successive tests, it would not become oxidized.

In addition, the provision of such a relatively large contact surface (with respect to the volume in which it is housed) ensures that the air stream passing through the mixing compartment evaporates (or takes) from the wicks' contact surface the required perfumery components that get mixed with the air stream thereby rendering a perfumed or scented air stream at the air outlet. This is even more noticeable in combination with above mentioned rather small mixing compartment as, due to the small volume, the air stream results in convective flows over the wick's outer surface that more easily extract the perfumery ingredients (i.e. not so volatile components) from the wick. This, in addition to above mentioned effects of having a rather small mixing compartment involves that successive tests produce substantially similar results, i.e. fidelity of successive tests are achieved or at least facilitated.

The provision of such a reduced mixing compartment (with respect to the wick's contact surface) thus involves that the perfumed air leaving the atomizer/diffuser outlet comprises more less volatiles components (e.g. perfumery components) than could have been e.g. in case of larger mixing compartments that, as explained above, may also house residual evaporated (most) and oxidized volatile components in between successive tests. This further contributes to avoiding or at least reducing the risk of saturation caused e.g. by smelling a perfume with a high content of alcohol.

Last but not least, the use an atomizer/diffuser substantially as herein disclosed needs a very low amount of liquid, e.g. the alcoholic or hydro-alcoholic perfume, for each test. As an example, it has been found that each test, i.e. for each pulse emitted by an air compressor sending an air stream to the inlet of e.g. approximately 25 ml to approximately 200 ml for a 5 seconds test, it uses around at least 0,1 mg of perfume, particularly around 1,5 mg to around 2 mg of perfume composition, depending on the perfume composition used.

In use, the air flow needed inside an atomizer substantially as hereinbefore describe may be defined as a function of the volume of mixing compartment such that it ensures at least 10 renewals of air flowing inside the mixing compartment in a second. In examples, at least 20 renewals/seg may be foreseen. In still more examples, at least 50 renewals/seg.

In some examples, the atomizer/diffuser may further comprise a central volume arranged surrounding or covering a portion of the wick extending into the liquid compartment. The central volume may extend from the mixing compartment opening to a bottom of the liquid compartment. In these cases, the atomizer may further comprise one or more flooding orifices providing fluid communication between the wick and an inside of the liquid compartment. The provision of a central volume surrounding the portion of the wick that extends into the liquid compartment enhances airtightness between the mixing compartment and the liquid compartment. This means that evaporation particularly of the highly volatile components of the liquid housed in the liquid compartment and flooding the wick is also avoided or at least reduced. The provision of the central volume surrounding the part of the wick extending into the liquid compartment further enhances transportation of a filled atomizer, i.e. an atomizer being transported full of liquid, e.g. an alcoholic or hydro-alcoholic perfume, as the central volume provides for the required airtightness to avoid or at least reduce undesired evaporations of the liquid from the liquid compartment to the mixing compartment.

In some examples, the atomizer/diffuser may further comprise a memory chip. This allows the atomizer to be mounted in e.g. perfume testers at the same time as information e.g. of the results derived from the atomizer or the type of perfume selected can be followed up by the user and/or can be programmed. Alternatively the memory chip allows communication e.g. through internet or a network using a suitable application. In more examples, other parameters that may be present in e.g. perfume testers may also be provided. Example of these other parameters may include duration of the test, air flow, air stream speed, temperature among others. In further examples, instead of a memory chip, the atomizer may be provided with a barcode, a serial number, a QR code or any other known means for recognition of the content housed inside the liquid compartment.

In some examples, the wick may traverse the entire mixing compartment. This way, the wick's contact surface substantially traverses the mixing compartment thereby removing e.g. in case of cylindrical wicks the end planar surface substantially parallel to an air stream sense of circulation. Orientation of the wick substantially perpendicular to the air stream sense of circulation enhances perfumery components extraction from the flooded wick.

In some examples, the wick may be formed of a plurality of absorbent material elements arranged not touching each other at least at the portion of the wick extending into the mixing compartment. This way, the contact surface of the wick results by adding an outer surface of each strip or cord. In some of these examples, the plurality of absorbent material elements may be selected from the group consisting of polyhedral shaped elements, strips or cords. In examples, the plurality of absorbent material elements may be arranged inside an imaginary circle. In alternative examples, wicks having other shapes may be foreseen, including wicks with ridges or other unevenness on their outer surfaces. Examples of wicks may comprise a cylindrical or a polyhedral wick.

In some examples, the mixing compartment may be cylindrical. In some of these examples in which the wick may also be cylindrical, an inner radius of the mixing compartment may range from 1% higher an outer radius of the wick to 100% higher the outer radius of the wick, particularly from 1% to 10%.

A further aspect provides a system comprising an atomizer substantially as hereinbefore described and a liquid in the liquid compartment, wherein the liquid comprises alcohol, particularly an alcohol-based perfume.

In another aspect a perfume tester is provided. The perfume tester comprises one or more atomizers substantially as hereinbefore described.

In some examples, the perfume tester may further comprise an air compressor configured to generate a pulsed air stream and solenoids or electro valves arranged at the atomizer air inlets and/or air outlets. In addition, a system for driving, controlling and selecting the atomizer to be used may further be provided.

In some examples, the perfume tester may comprise an air filter arranged between the air compressor and the atomizer air inlets. In more examples, drop traps may further be provided at the atomizer air outlets to prevent the passage of drops in the outgoing air stream. In more examples, an ozone generator device may further be provided for maintenances and/or deodorizations in between liquid (perfume) changes. In examples, an air heater may be provided, e.g. at the exit of the air filter, for adjusting a temperature of the air stream.

Perfume testers substantially as described may further include the same or different perfumes in each liquid compartment, wherein the perfumes comprise alcohol. Put in other words, the liquids are alcohol-based perfumes.

As further explanation, the perfume testers disclosed herein are based on the incorporation of one or more atomizers as herein disclosed. In other words, it consists of a device that integrates the following main elements:

A. One or more refillable atomizers, each provided with a memory chip for individual use, in which the contact between the air stream and the perfume may be carried out, as a main body provided with air input from the outside and a perfumed air outlet based on the arrangement of its three main and differentiated compartments, one configured to house the perfume at a lower level, another configured to house a cotton or similar connected to the first one by small holes through which the perfume accesses impregnating the cotton in its entirety by capillarity, and a third compartment located above the first one and configured such that the air stream circulates, running into the walls of the aforementioned cotton in its way towards outside, which by contact/friction transforms it in perfumed air B. Air filter for purifying the air entering to the device.

C. Air compressor generating the air stream. For example an air compressor configured to generate pressures over approximately 2Kpa.

D. Solenoids or electro-valves both at the entrance and at the exit of each atomizer in order to provide tightness and prevent the perfume from evaporating. In addition, they may act as switches for the air flow of the different perfumes installed.

E. Droplet trap that prevents the passage of the same with the air stream towards the outlet conduit.

F. Interconnection pipes.

G. One or more orifices, depending on the model of the perfumed airflow outlet towards the outside of the equipment.

H. System for driving, controlling and selecting of the perfume to be tested.

I. Power source or sources for the different elements.

J. Ozone generator for maintenance and deodorization of the device in between perfume changes.

K. Heating element for controlling air stream temperature.

From the described assembly, its operation is achieved by deploying the following sequence of operations;

A. Process of selection of the perfume to be tested by the user consisting of a series of buttons associated with the product image or through a program or application that allows access to the different products through a touch screen or similar.

B. Pressing the component according to a button or digital panel that indicates the beginning of a test.

C. Recognition of the product in question by reading the memory incorporated in the atomizer itself, reading or recognizing barcode, serial number or data entered in the equipment itself or compiled by network or internet connection.

D. Adjustments of the different parameters according to the previous reading consisting of regulating the air flow, air temperature, testing times, and even controlling the condition of the perfume, preventing the test if it has exceeded the time established since its installation or it has exceeded the number of maximum programmed tests.

E. Launching of the product image, features, sounds, multimedia, attending to the data or reading information.

F. Activation of the selected perfume solenoids from closed to open positions.

G. Activation of indicators that indicate to the user the beginning of the test.

H. Activation of the air heater according to preset adjustments according to data or reading information.

I. Activation of the air compressor according to preset adjustments according to data or reading information.

J. Activation with or without timing of the test according to preset adjustments according to data or reading information.

K. End of the time at the end of the timer or when releasing the pushbutton if there is no timer.

L. Stopping the air compressor.

M. Stopping the solenoids.

N. Stopping or actuating of indicators that indicate to the user the completion of the test.

Thus, in conclusion, the "perfume tester based on the incorporation of one or more atomizers" provides the following advantages with respect to the state of the art:

A. Avoiding the high volatility of the perfume by making use of three volumes inside each atomizer. A first larger volume where the perfume in liquid state may be housed and that may allow a greater expansion of the gas caused by the volatile components. A second intermediate volume which may contain an absorbent material such as cotton, and a much smaller third volume in which the perfume may not flood the space but may be in contact with it through its walls that may be at least partially formed of the aforementioned cotton or some synthetic fiber or similar that do not add odours to the perfume itself.

B. Contact of the air stream with the perfume in a gentle manner, by passing the air stream through the third volume of the aforementioned atomizer arranged so as to cause a proper friction with its cotton walls impregnated with perfume.

C. Avoiding excess of alcohol in the mixture with the air as the air may only circulate through the cavity having smaller volume (i.e. the mixing compartment), while the atmosphere (liquid compartment) of greater volume where the more volatile compounds would more easily expand is isolated by the barriers placed by tubes in an adequate arrangement and serving as insulation of the cotton impregnated with the perfume. In addition, the air may cause a pressure contrary to that of the vapours preventing the mixture with these as well as the exit of said vapours to the outside.

D. Avoiding liquids in the mixture thanks to the own layout of the different elements, the gravity and the own direction and sense of circulation of the air that causes an opposite pressure to the liquid or vapours, avoiding the liquids from being dragged by the air. As an additional measure, a trap for liquids may be incorporated at the air outlet, which may consist of a kind of cap on which it would collide and it may then return to the container, it may even be disposed inside the atomizer itself.

E. Purifying the incoming air by means of appropriate filters, preventing that in a typical environment of a perfume store where the air is contaminated with odors it may be added to the perfume to be tested, thereby altering its original smell.

F. Adjusting the mixture using the following parameters:
Absorbent material to be used e.g. cotton, synthetic material.
Density of absorbent material to be used e.g. cotton more or less dense or tight.
Greater or lesser path through the cavity e.g. longer, zig-zag, double path up-down-up.
Greater or lesser friction of the air in contact with the cotton e.g. narrower or wider cavity.
Insulating material between cotton and air passage. A physical barrier may be provided that causes more or less contact with the air, for example, a mesh or a micro perforated sheet.
Cotton having a ridged shape or some other that causes more friction (an enlarged contact surface) e.g. in the shape of a snake or conical.

G. Possibility of adjusting the air flow through valves or on the compressor or air pump.

H. Temperature adjustment by using a heater that heats the air in its way.

I. Avoiding mixtures of the different perfumes: all stages may be separated except for the generation of air that may be common to all as it is not in contact with the perfumes. The outlets may be treated separately, but they may also be unified in a single exit point trying to reduce to a minimum its path but warning that in this design there would be a mixture of smells although it would be minimal and negligible for a user. To avoid this mixture as much as possible, appropriate materials may be used, mainly PTFE (Teflon®), which have excellent properties for these purposes, i.e. it has a rather low absorption and/or friction coefficients. In addition, ozone gas technology to deodorize said common areas, when required, and that do not transcend throughout its use or when facing a fragrance substitution, may be used.

J. Possibility of equalising the test: this section is given by the features of the atomizer, if the same features are used for a particular perfume where the previously commented adjustments have been set according to the preferences and tests carried out by a perfumer, manufacturer or others, the tests carried out in the different establishments may be equalised. In addition, other factors, external to the atomizer, may also determine the result or the perception of the test, for example:
Adjustment of air flow
Adjustment of air temperature
Condition of the perfume according to its date of packaging.
Number of tests performed with the same atomizer since its installation date.
Corporate image such as description, sounds, multimedia image, etc.

In this respect, a system for recording these parameters, product data and images or others if required and that are subsequently read and processed by the device is disclosed as a solution. This way it is ensured that a perfume is tested in the desired way and with an adequate durability in order to be uniform throughout its lifetime, considering that perfumes lose properties over time and much more if they are wrongly preserved.

K. Simplicity for the manufacturer or creator: they may only have to select a type of atomizer and record the adjustment parameters in its memory according to one selected from the group consisting of a memory chip incorporated in the atomizer itself, codes of bars, QR codes, serial numbers or others. These may be the most advanced extremes, but the merchant or operator may also prescribe it and have it programmed. Another option is to communicate through internet using an application created for this purpose. In any case, it is about having the maximum connoisseurs of the product to control the process and the quality of the test.

L. Simplicity for the merchant: here the ease refers to manipulating the device. To do this it may be enough to insert an atomizer in a simple manner or without entailing cumbersome adjustments.

M. Simplicity for the end user: it may be limited to testing perfumes instantly and with the best conditions, quickly, without saturation and with quality which may allow a correct evaluation of the different tested options.

N. Conservation of the perfume: direct contact with the external atmosphere is avoided due to the arrangement of the perfume in a cavity (liquid compartment) other than the one (mixing compartment) that causes friction/contact with the air. In addition, all cavities are kept watertight by means of suitably arranged solenoids. This way, oxidation and volatility of the perfume are avoided, or at least reduced.

O. Considerable saving of perfume compared to traditional test: the average consume of a traditional test performed by direct pulsation of the perfume container itself, varies between 50 and 200 μL, with our design the consumption would be reduced in at least 50 times. Besides allowing saving perfume a clear advantage refers to not having to replace them frequently.

BRIEF DESCRIPTION OF THE DRAWINGS

Non-limiting examples of the present disclosure will be described in the following, with reference to the appended drawings, in which.

Figure 1:
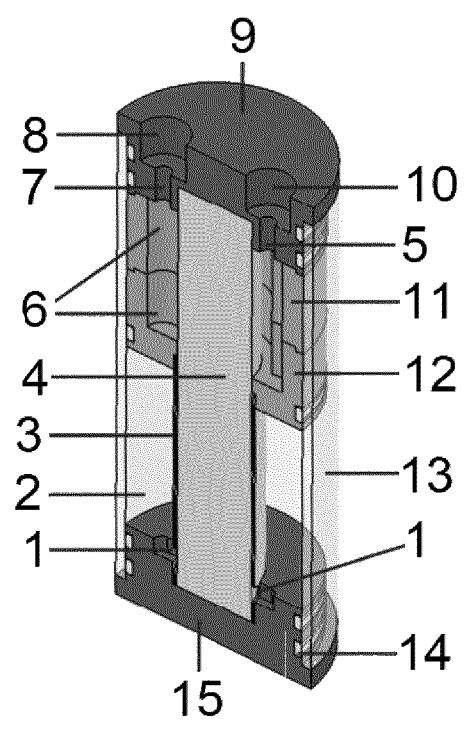
FIG. 1 shows a perspective view of the main section of an atomizer according to an example.

In the mentioned figures the following elements may be highlighted:

1. Contact or flooding orifices between the stored perfume and the cotton arranged in the central volume
2. Liquid or perfume compartment or cylindrical wall compartment where the perfume is deposited
3. Wick compartment or cylindrical tube or central volume
4. Wick or cotton housed in the wick compartment generated by the cylindrical tube, as well as in the upper mixing compartment
5. Internal orifice through which the air stream exits from the upper mixing compartment to the outside
6. Mixing compartment or upper compartment configured to direct the air stream to be perfumed by mixing by friction/contact with an outer contact surface of the wick or cotton
7. Interior orifice through which outside air accesses the upper mixing compartment
8. External orifice through which outside air accesses the upper mixing compartment and which is also responsible for connecting to the rest of the assembly by means of a quick snap connection
9. Top cover of the assembly
10. External orifice through which the air exits from the upper or mixing compartment towards the outside and which is also responsible for connecting the rest of the assembly by means of a quick snap connection 27.
11. Upper casing of the mixing compartment
12. Lower casing of the mixing compartment
13. Outer wrapping tube of the assembly
14. Gaskets.
15. Bottom cover of the assembly through which perfume replenishment may additionally be carried out
16. Atomizer
17. Air filter
18. Air compressor
19. Solenoids or electro-valves
20. Drops trap
21. Interconnection pipes
22. Ozone generator
23. Check valve
24. Heating device
25. Exit or outlet to the outside
26. Operation control or activation buttons
27. quick snap connector atomizer-equipment
100 Bar showing the percentage of Alpha-isomethyl ionone over Limonene in a typical prior art atomizer
101 Bar showing the percentage of Iso E Super ver Limonene in a typical prior art atomizer
200 Bar showing the percentage of Alpha-isomethyl ionone over Limonene in an atomizer as disclosed herein
201 Bar showing the percentage of Iso E Super ver Limonene in an atomizer as disclosed herein.

DETAILED DESCRIPTION OF EXAMPLES

Throughout the following figures the same reference numbers will be used for matching parts.

Figure 3:
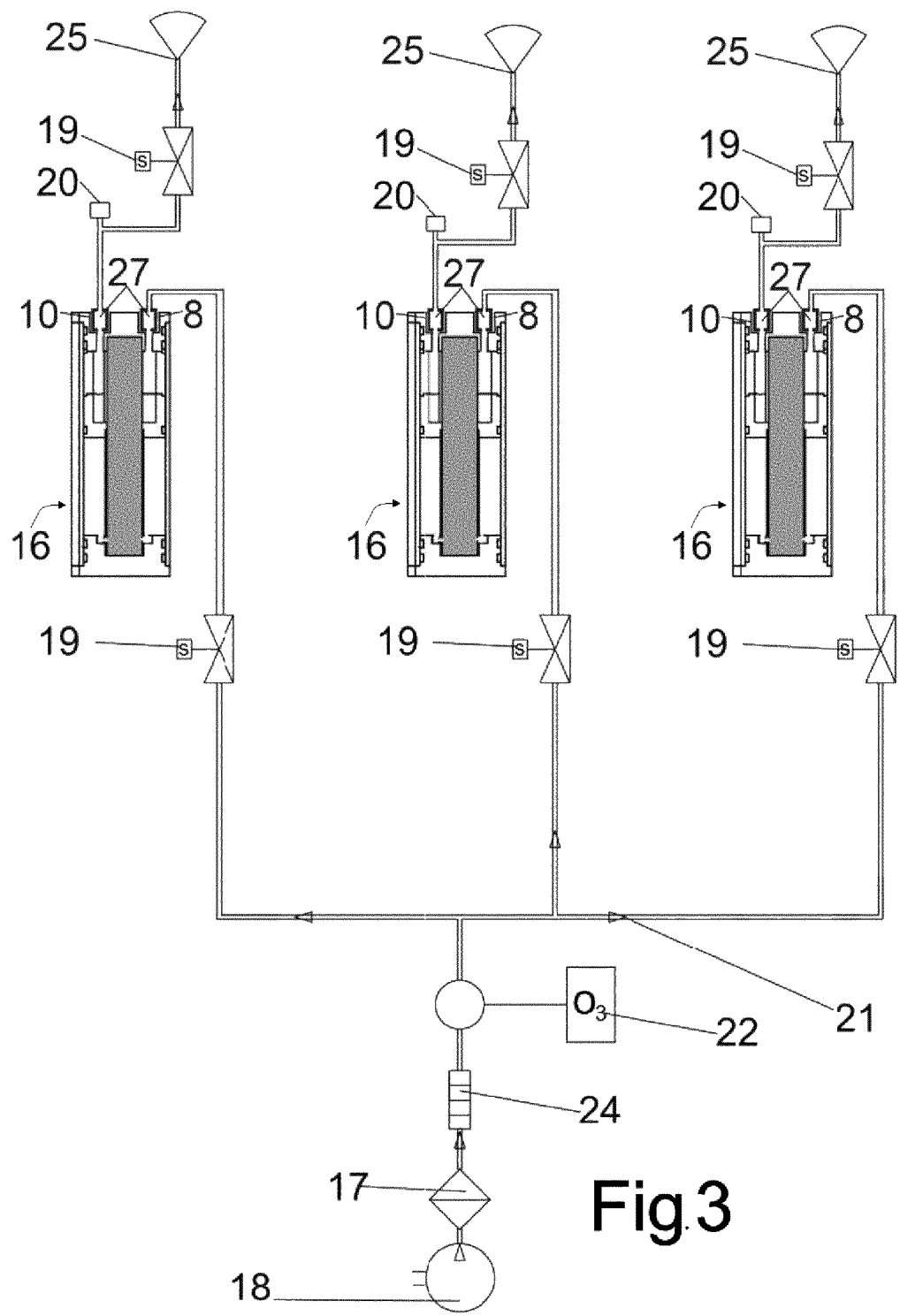
FIG. 3 shows a perfume tester comprising one or more atomizers according to an example.

FIG. 3 shows an example of a perfume tester comprising three atomizers 16 with independent outlets 25 and a flow control by means of solenoids 19. In alternative, other number of atomizers may be foreseen. In this example the perfume tester comprises:

A. Three atomizers 16 as those shown in FIGS. 1-2, arranged according to three main and differentiated compartments 2, 3 and 6, a lower liquid e.g. perfume compartment 2 being in the form of an exterior involute designed to contain the perfume, while a cylindrically shaped interior compartment or central volume 3 contains the wick or cotton 4 that is impregnated of the perfume in its entirety by capillarity when in contact with it through respective flooding orifices 1 and, an upper mixing compartment 6 arranged free of perfumes and only interacting with the perfume by contact with outer walls of said wick or cotton 4 in its upper part arranged in the central volume 3.

Finally, the cylindrical tube (central volume 3) acts as a cover or casing for the cotton 4 thereby avoiding or at least reducing possible deformations of the cotton 4 and that the perfume flooding the exterior involute (liquid or perfume compartment 2) gets in contact in its whole surface directly with the cotton 4 arranged in the central volume (central volume 3), also acting as a more effective barrier for the vapors. As explained above, the central volume provides for a barrier or airtightness for vapours that may evaporate from the perfume (liquid) compartment towards the mixing compartment.

Being the main element of the disclosure that would be completed with the corresponding sealing gaskets that prevent the perfume from being moved to other unwanted compartments, in order to facilitate its understanding, its operation would consist in that once the perfume to be tested is housed in the lower involute (perfume compartment 2), it passes through the flooding orifices 1 to the central volume 3 and by capillary action it rises and impregnates the walls of the cotton 4 housed therein throughout its surface until it becomes present through the outer walls of the cotton 4 in the upper mixing compartment 6. Thus, with the activation of the test, forced air is introduced through the external orifice 8 forcing a friction with the walls of the cotton 4 impregnated with perfume, to drive the air naturally towards a single external orifice 10 once it has been in contact with the perfume.

Figure 2:
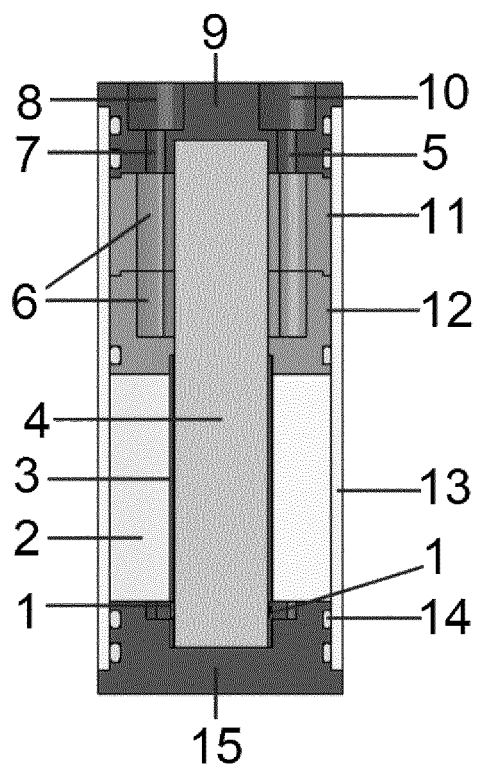
FIG. 2 shows an elevation view of the main section of the atomizer of FIG. 1.

Depending on the contact surface of the air moving through the upper mixing compartment 6 with the walls of the cotton 4, may thus define the perfume's density in the air stream, so that the dimensions may be adjusted as a function of the needs or preferences. In the example of FIGS. 1-2, two elements or casings 11 and 12 are shown. Density adjustment may thus be carried out by removing e.g. the casing 11 or by incorporating an additional one thereby rendering a larger or smaller mixing compartment according to circumstances.

B. Air filter 17 to avoid the characteristic odor of a saturated atmosphere existing in perfumeries or other establishments dedicated to the sale of these products, consisting of an odor filter that for example may be based on activated carbon.

C. Air compressor 18 able to develop an adequate air flow for the volume of perfumed air that is to be transferred to the user, mainly according to parameters of distance at which the user is placed and even the sensation or intensity that is to be transmitted. For example, for a distance close to the device, i.e. between 10 cm and 30 cm, a flow between approximately 5 ml/seg and approximately 40 ml/seg would be sufficient. Particularly, air flows of approximately 12 ml/seg may be foreseen. Such flows are substantially similar to a nasal inhalation, i.e. a perfume test. It is also important to take into account the size of the perfumed air outlet orifice 25, needing more air flow for a larger size of it to release the air at the same distance. For the previous example, a diameter between 1 mm and 3 mm may be used. In addition, to increase the production capacity of the compressor in those cases in which there is regulation, since e.g. it allows making an upward adjustment according to the preferences that are set in each case. The air compressor is configured to work in a pulsed manner.

D. Solenoids 19 or electrovalves both at the entrance and the exit of each atomizer 16 in order to provide tightness and prevent the perfume from evaporating.

E. Drops trap 20 arranged at the exit of the atomizer, or alternatively inside it avoiding contamination of external elements based on a suitable design of said atomizer.

F. Interconnecting pipes 21 preferably in PTFE (Teflon®) compound to conduct air through the various elements.

G. Outlet orifice 25 with an approximate diameter varying between 0,5 mm and 3 mm arranged in one or more, according to design from where the perfumed air is thrown to the outside, generating a stream with a sufficient flow to throw it an adequate distance so that it is smelled by the user according to the adjustment criteria and that it does not have to be mixed in excess with the outside air so that it reaches the nose of the user as pure as possible.

H. Controls according to multiple possibilities from a simple button that activates each outlet to a more complex electronic or computer equipment.

I. Power supplies adapted to the supply voltages of the different elements DC 12V, 5V etc.

J. Ozone generator 22 for exclusive use in maintenance work and replacing one perfume with another in order to deodorize.

K. Heater 24 for controlling the temperature of the air stream.

Figure 4:
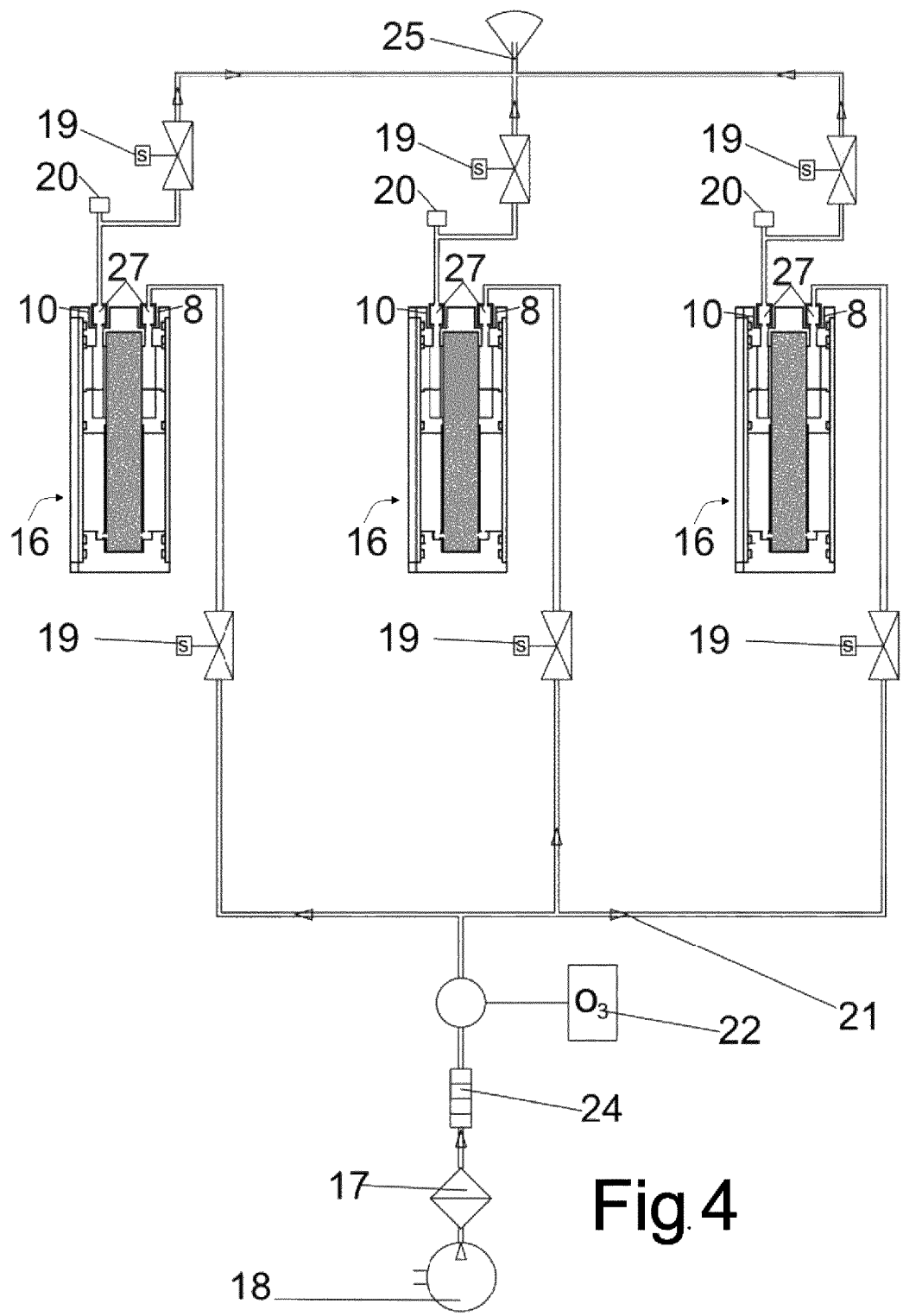
FIG. 4 shows a perfume tester according to another example.
Figure 5:
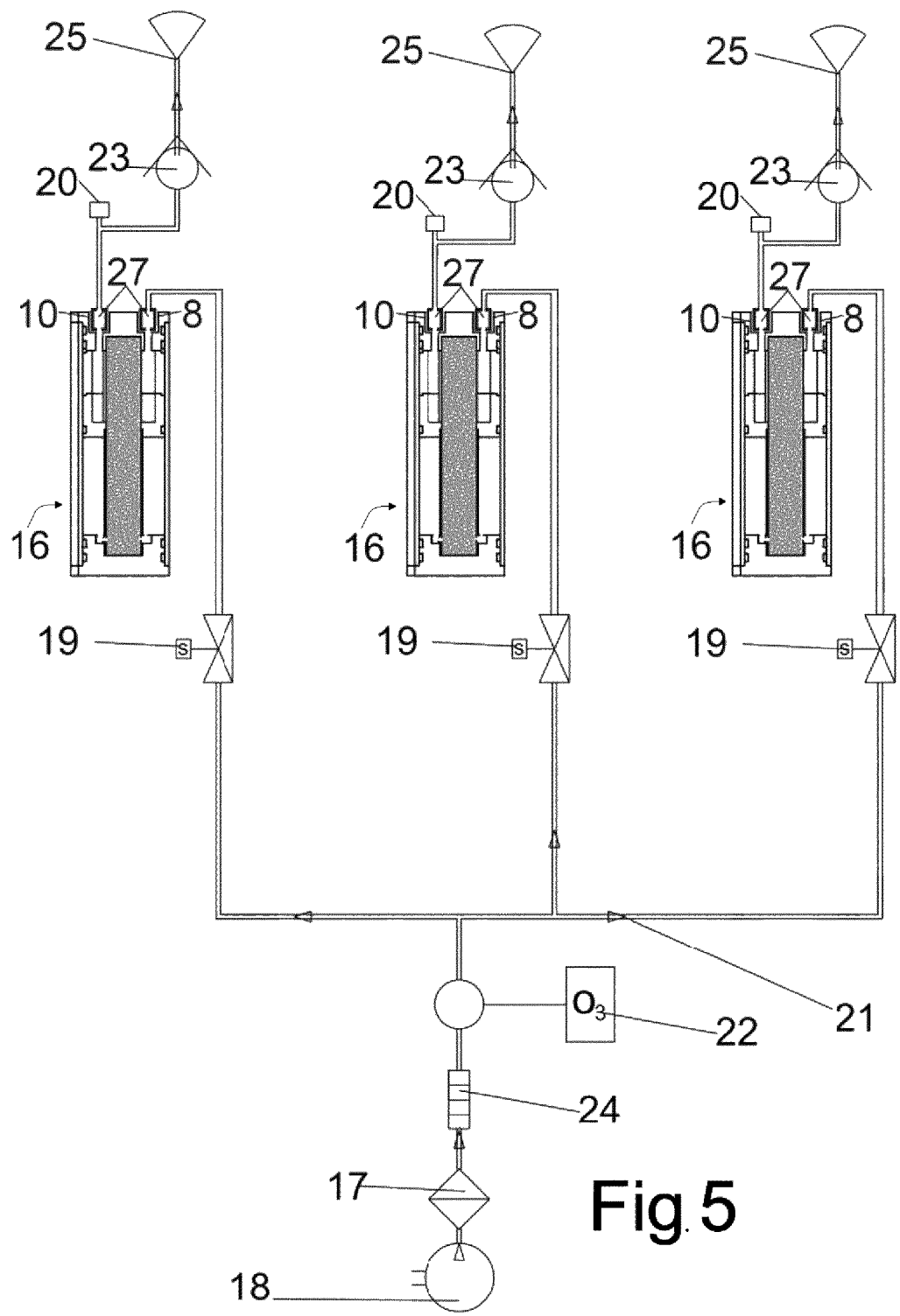
FIG. 5 shows a perfume tester according to a still further example.

Alternatively, the above described device may be conceived in a completely analogous manner even though mounting a single common outlet 25 of the perfume towards the outside as shown in FIG. 4. Likewise, as an alternative example, as shown in FIG. 5, the outlet solenoid could be replaced by a check valve 23 allowing air flow in a direction under a pressure greater than that which would be caused by the perfume vapor itself.

From the elements described, and in order to further facilitate the understanding of the present disclosure its overall operation implemented according to FIG. 3 would be approached by displaying the following sequence:

1. Pressing the component according to a button or digital panel that indicates the beginning of a test.

2. Recognition of the product in question by reading the memory chip incorporated in the atomizer itself, reading or recognizing barcode, serial number or data entered in the equipment itself or collected by network or internet connection.

3. Adjustments of the different parameters according to the previous reading, consisting of regulating the air flow, air temperature, test times, sending sounds, images and product data, and even controlling the state of the perfume, preventing the test if the time established since its installation is exceeded or the maximum number of tests has been exceeded.

4. Activation of the selected perfume solenoids, moving from closed to open positions.

5. Activation of indicators that indicate to the user the beginning of the test.

6. Activation of the air compressor pulsation. Alternatively, if the referred compressor has power adjustment, this would be carried out previously.

7. Timing of the test during the established time. Alternatively, the operation of the test may be considered while the button is being pressed. In this respect, the device must have indications for the user to be positioned correctly.

8. Ending of the time at the end of the timer or when releasing the pushbutton if it does not have a timer.

9. Stopping the air compressor.

10. Stopping of the solenoids.

11. Stopping or actuating of the indicators that indicate to the user the completion of the test.

Alternatively, it is possible to conceive designs of the atomizer based on the same principle of operation although presented with different terminations;

Entry and exit of air through the top portion.

Entry and exit of the air stream through the bottom portion.

Crossed air stream entries upwards or downwards.

Double or more vertically or horizontally air path.

With or without a perfume filling orifice depending on whether it is intended for single use or multiple uses.

Facilitating the replacement of the entire central part that allows changing the cotton and thus being able to change the perfume or simply for replacement due to deterioration or wear.

Varied geometries, not necessarily cylindrical.

Figure 6:
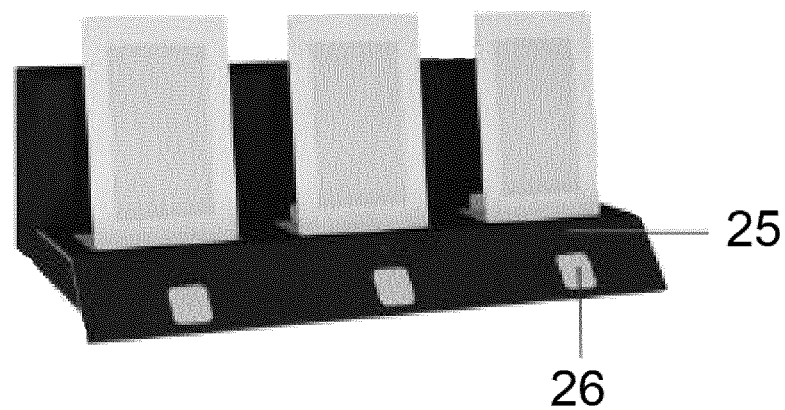
FIG. 6 shows the perfume tester of any of FIG. 3 or 5 with multimedia screen to show product image.
Figure 7:
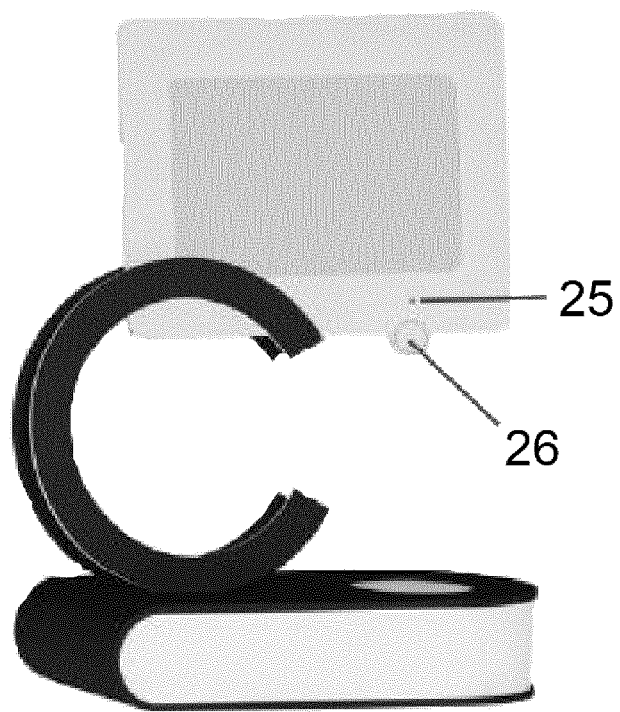
FIG. 7 shows a perfume tester comprising a single perfume test device with a multimedia screen to show the product image.
Figure 8:
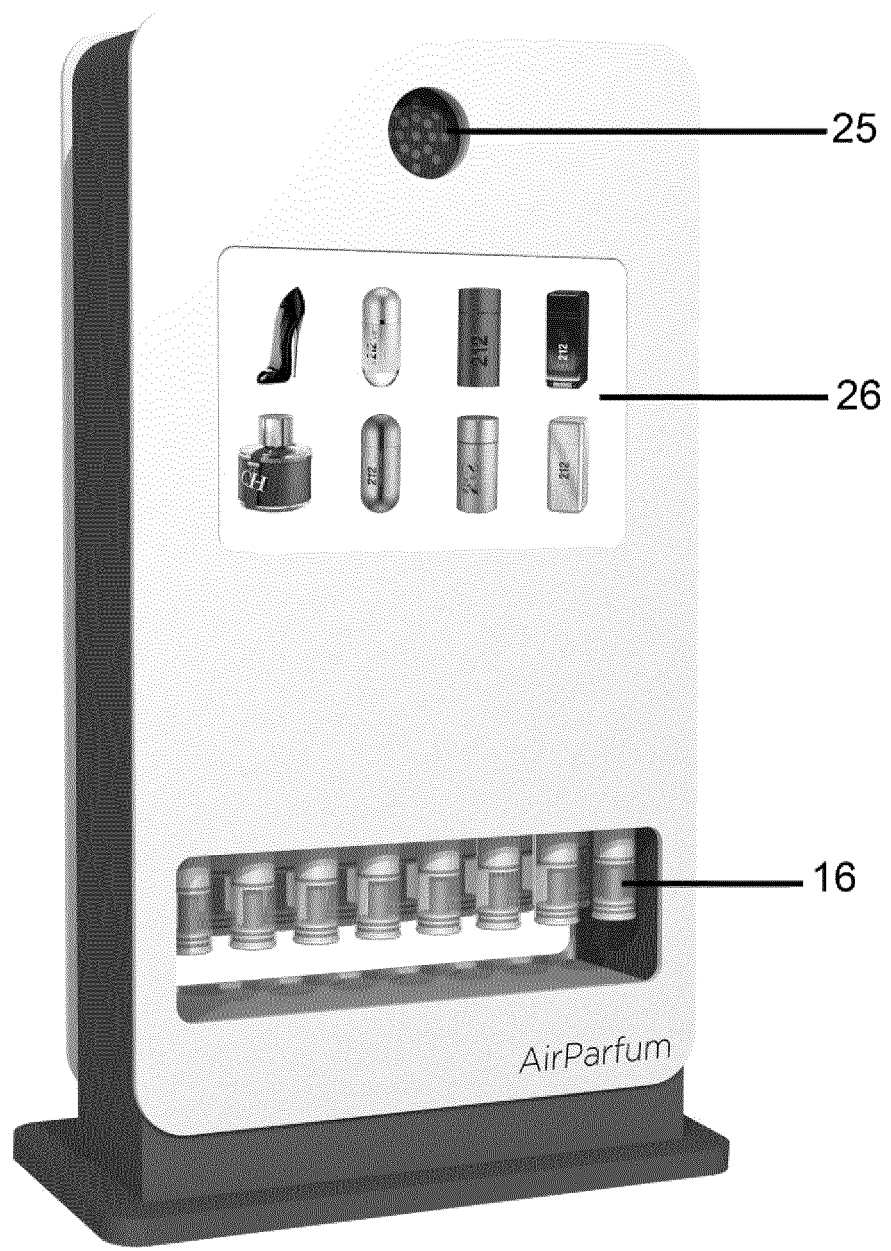
FIG. 8 shows a perfume tester for sixteen perfume atomizers according to the example of FIG. 4 supported in a computer application.

Finally, in case of integrating a computer application into the operation of the system, it would be possible to record specific data such as brand, name, description, images, videos, expiration, etc., and even record on it other data such as the date of installation, time of use, remaining time of use, all kinds of adjustments and others that may serve not only to control each test but to optimize the use in terms of reliability and simplicity presenting the product according to a wide range of possibilities as it is appreciated in FIGS. 6-8 that one or more activation buttons 26 may be provided and an orifice or set of orifices 25 through which the perfumed air flow exits to the outside are shown.

Alternatively, the atomizer may be designed without the tube 3 containing the cotton and, consequently, the connection orifices 1, the operation being entirely analogous.

Figure 9:
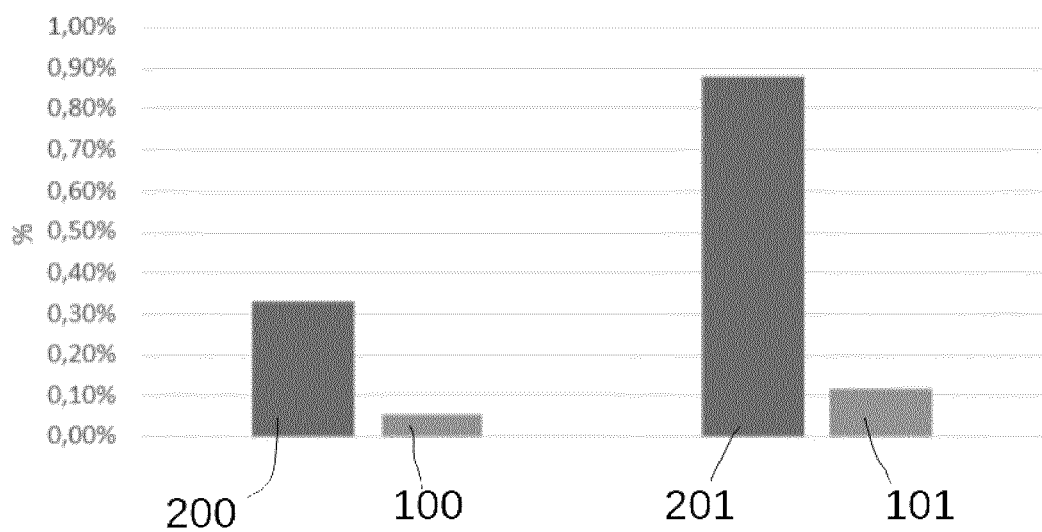
FIG. 9 shows in a very general manner a comparison of the ratio of typical examples of perfumery ingredients when a test is performed in typical atomizers versus in an atomizer substantially as herein disclosed.

FIG. 9 shows a comparison of the ratio of Alpha-isomethyl ionone and Iso E Super over Limonene which are typical perfumery ingredients in typical atomizers versus in an atomizer substantially as herein disclosed. Bars 100 and 101 respectively show the percentage of Alpha-isomethyl ionone over Limonene and Iso E Super over Limonene present in a test carried out in a typical prior art atomizer. Bars 200 and 201 respectively show the percentage of the same ingredients, Alpha-isomethyl ionone and Iso E Super over Limonene, present in a test carried out in an atomizer substantially as herein before described.

Generally, the comparison between bars 200 and 100 show that Alpha-isomethyl ionone/Limonene which is usually (in prior art atomizer) present in around 5% now raises to around 30% thereby increasing around six times its presence which indeed results in a surprising olfactory test. Comparing now bars 201 and 101 it is shown that Iso E Super/Limonene increases around 8 times when one test a perfume using an atomizer as described herein. From around 10% present when the test is carried out in a typical atomizer to around 80% when the test is carried out in an atomizer as described herein.

This is explained due to the relatively large wick contact surface in combination with the relatively small volume of mixing compartment as explained above. This way, the air stream flowing in such a small volume results in a convective flow that more easily extracts not so volatile components (i.e. perfumery ingredients) from the flooded wick contact surface (of a relatively large size with respect to the volume of the mixing compartment.

It is not considered necessary to make this description more extensive so that any expert in the field understands the scope of the disclosure and the advantages derived therefrom. The fact that the drop trap is conceived at the exit of the atomizer or inside it, the materials chosen for the manufacture of the different elements, dimensions, thicknesses, design, implementation of the same or way of connecting them, etc., will be susceptible of modification as long as it does not imply an alteration of the essence of the disclosure.

The terms in which this report has been written should always be taken in a broad and non-limiting sense.

For reasons of completeness, various aspects of the disclosure are set out in the following numbered clauses:

Clause 1. Perfume tester based on the incorporation of one or more atomizers, wherein its refillable atomizers inside which contact between the air stream and the perfume will be carried out, each equipped with a memory chip for individual use, and designed as a main body provided with air intake from the outside and a perfumed air outlet, based on the layout of its three main and differentiated compartments, one designed to house the perfume at a lower level, another designed to house a cotton or similar connected to the first by one or more small orifices through which the perfume accesses impregnating the cotton in its entirety by capillarity, and a third compartment located above the first and designed such that the air stream circulates through it finding on its way towards the outside walls of the aforementioned cotton that turn the air stream into perfumed air.

Clause 2. Perfume tester based on the incorporation of one or more atomizers according to clause 1, wherein alternatively, each atomizer may be configured by removing the tube that provides containment for the cotton or similar, so that the cotton is housed by its base directly on the lower compartment containing the perfume, removing the connecting ducts between the two compartments, while the air stream circulates around an upper compartment that contours the cotton contacting the perfume through the walls of the cotton impregnated with the liquid analogously by capillarity.

Clause 3. Perfume tester based on the incorporation of one or more atomizers, according to clauses 1 and 2, wherein it is carried out based on the integration of said atomizers with the following main elements:

A. Air filter for purification of the air accessing to the device;

B. Air compressor generating the air stream;

C. Solenoids or electro valves both at the entrance and exit of each atomizer in order to make tightness and prevent the perfume from evaporating; they will also act as switches for the air flow of the different perfumes installed.

D. Drop trap that prevents the passage of the same with the air stream towards the outlet conduit;

E. Interconnection pipes;

F. One or more exit orifices of the air stream to the outside;

G. System for driving, controlling and selecting of the perfume to be tested;

H. Power supplies;

I. Ozone generator for device maintenance and deodorization in between perfume changes;

J. Air heater element to adjust to the desired temperature.

Clause 4. Procedure of using the perfume tester based on the incorporation of one or more atomizers according to clauses 1, 2 and 3, wherein its operation is based on the following sequence of operations:

A. Process of selection of the perfume to be tested by the user consisting of a series of buttons associated with the product image or through a program or application that allows access to different products through a touch screen or similar;

B. Pressing the component according to button or digital panel that indicates the beginning of a test;

C. Recognition of the product in question by reading the memory incorporated in the atomizer itself, reading or recognizing barcode, serial number or data entered in the equipment itself or compiled by network or internet connection;

D. Adjustments of the different parameters according to the previous reading consisting of regulating the air flow, air temperature, test times, and even controlling the condition of the perfume, preventing the test if it has exceeded the time established since its installation or it has exceeded the maximum number of scheduled tests;

E. Launching of the product image, features, sounds, multimedia, attending to the data or reading information;

F. Activating the solenoids of the selected perfume going from closed to open position;

G. Activating the indicators that indicate to the user the beginning of the test;

H. Activating the air heater following preset adjustments according to data or reading information;

I. Activating the air compressor following preset adjustments according to data or reading information;

J. Activating with or without timing the test following preset adjustments according to data or reading information;

K. Ending time at the end of the timer or when releasing the pushbutton if it does not have timer;

L. Stopping the air compressor;

M. Stopping the solenoids;

N. Stopping or activating indicators indicating to the user the completion of the test.

Clause 5. Perfume tester based on the incorporation of one or more atomizers according to clauses 1, 2, 3 and 4, wherein alternatively, the outlet solenoid may be replaced by a check valve allowing the air flow in the direction of circulation of air towards the outside under a pressure higher to that provoked by the vapor of the perfume itself.

Clause 6. Atomizer for alcoholic or hydro-alcoholic liquids comprising:
- a liquid compartment configured to receive a liquid; and
- a mixing compartment provided next to the liquid compartment, the mixing compartment comprising an air inlet and an air outlet;
- wherein the mixing compartment comprises a mixing opening facing the liquid compartment and the liquid compartment comprises a liquid opening facing the mixing compartment, wherein the mixing opening matches the liquid opening; and the atomizer further comprises
- a wick connecting the liquid compartment and the mixing compartment such that in use the wick fits in the liquid compartment opening and in the mixing compartment opening in an airtight manner, the wick extending into the mixing and liquid compartments,
- wherein a portion of the wick extending into the mixing compartment comprises an outer contact surface and a volume of the mixing compartment is defined such that a ratio between the outer contact surface and the volume of the mixing compartment is at least approximately 0.05 mm$^{-1}$; particularly at least approximately 0.4 mm$^{-1}$, more particularly at least approximately 1:1.

Clause 7. Atomizer according to clause 6, further comprising a central volume arranged surrounding a portion of the wick extending into the liquid compartment, the central volume extending from the mixing opening to a bottom of the liquid compartment and the atomizer further comprises one or more flooding orifices providing fluid communication between the wick and an inside of the liquid compartment.

Clause 8. Atomizer according to clauses 6 or 7, further comprising a memory chip.

Clause 9. Atomizer according to any of clauses 6-8, wherein the wick traverses the entire mixing compartment.

Clause 10. Atomizer according to any of clauses 6-9, wherein the wick traverses the entire liquid compartment.

Clause 11. Atomizer according to clause 10, wherein the flooding orifices are provided at or near a bottom of the liquid compartment.

Clause 12. Atomizer according to any of clauses 6-11, wherein the wick is formed of a plurality of absorbent material elements arranged not touching each other at least at the portion of the wick extending into the mixing compartment other.

Clause 13. Atomizer according to clause 12, wherein the absorbent material elements are selected from the group consisting of polyhedral shaped elements, strips or cords.

Clause 14. Atomizer according to any of clauses 6-13, wherein the wick is cylindrical.

Clause 15. Atomizer according to clause 14, wherein the mixing compartment is also cylindrical, an inner radius of the mixing compartment ranging from 1% higher an outer radius of the wick to 100% higher the outer radius of the wick, particularly from 1% to 10%.

Clause 16. Atomizer according to any of clauses 6-15, wherein the liquid compartment comprises an openable bottom so as to allow refilling the liquid compartment.

Clause 17. System comprising the atomizer of any of clauses 6-16 and a liquid in the liquid compartment, wherein the liquid comprises alcohol, particularly an alcohol-based perfume.

Clause 18. Perfume tester comprising one or more atomizers according to any of clauses 6-16.

Clause 19. Perfume tester according to clause 18, further comprising an air compressor configured to generate a pulsed air stream and solenoids or electro valves arranged at the atomizers air inlets and/or air outlets.

Clause 20. Perfume tester according to clauses 18 or 19, further comprising a system for driving, controlling and selecting the atomizer to be used.

Clause 21. Perfume tester according to any of clauses 18-20, further including the same or different perfumes in the liquid compartments, wherein the perfumes are alcohol-based perfumes.

The invention claimed is:

1. A perfume tester comprising one or more atomizers for atomizing an alcohol-based liquid perfume, the one or more atomizers comprising:
   - a liquid compartment configured to receive the alcohol-based liquid perfume; and
   - a mixing compartment provided next to the liquid compartment, the mixing compartment comprising an air inlet and an air outlet;
   - wherein the mixing compartment comprises a mixing opening facing the liquid compartment and the liquid compartment comprises a liquid opening facing the mixing compartment, wherein the mixing opening matches the liquid opening; and the atomizer further comprises
   - a wick connecting the liquid compartment and the mixing compartment such that in use the wick fits in the liquid compartment opening and in the mixing compartment opening in an airtight manner, the wick extending into the mixing and liquid compartments,
   wherein a portion of the wick extending into the mixing compartment comprises an outer contact surface and a volume of the mixing compartment is defined such that a ratio between the outer contact surface and the volume of the mixing compartment is at least 0.05:1.

2. The perfume tester according to claim 1, wherein the ratio between the outer contact surface and the volume of the mixing compartment is at least 0.4:1.

3. The perfume tester according to claim 1, wherein the ratio between the outer contact surface and the volume of the mixing compartment is at least 1:1.

4. The perfume tester according to claim 1, further comprising a central volume arranged surrounding a portion of the wick extending into the liquid compartment, the central volume extending from the mixing opening to a bottom of the liquid compartment and the atomizer further comprises one or more flooding orifices providing fluid communication between the wick and an inside of the liquid compartment.

5. The perfume tester according to claim 1, further comprising a memory chip.

6. The perfume tester according to claim 1, wherein the wick traverses the entire mixing compartment.

7. The perfume tester according to claim 1, wherein the wick traverses the entire liquid compartment.

8. The perfume tester according to claim 4, wherein the one or more flooding orifices are provided at a bottom of the liquid compartment.

9. The perfume tester according to claim 1, wherein the wick is formed of a plurality of absorbent material elements, the absorbent material elements being arranged not touching each other at least at the portion of the wick extending into the mixing compartment.

10. The perfume tester according to claim 9, wherein the absorbent material elements are selected from the group consisting of polyhedral shaped elements, strips, and cords.

11. The perfume tester according to claim 1, wherein the wick is cylindrical.

12. The perfume tester according to claim 11, wherein the mixing compartment is cylindrical, an inner radius of the mixing compartment ranging from 1% greater than an outer radius of the wick to 10% greater than the outer radius of the wick.

13. The perfume tester according to claim 1, wherein the liquid compartment comprises an openable bottom so as to allow refilling the liquid compartment.

14. A system comprising the perfume tester of claim 1 and a liquid in the liquid compartment, wherein the liquid comprises an alcohol-based liquid perfume.

15. The perfume tester according to claim 1, further comprising an air compressor configured to generate a pulsed air stream and solenoids or electro valves arranged at the atomizers air inlets and/or air outlets.

16. The perfume tester according to claim 1, further comprising a system for driving, controlling and selecting the atomizer to be used.

17. The perfume tester according to claim 1, further including the same or different perfumes in the liquid compartments, wherein the perfumes are alcohol-based perfumes.

* * * * *